United States Patent
Kang et al.

(10) Patent No.: US 10,466,219 B2
(45) Date of Patent: *Nov. 5, 2019

(54) VAPOR SENSOR SUITABLE FOR DETECTING ALCOHOLIC RESIDUE AT A SKIN SITE

(71) Applicant: 3M INNOVATIVE PROPERTIES COMPANY, St. Paul, MN (US)

(72) Inventors: Myungchan Kang, Woodbury, MN (US); Michael C. Palazzotto, Woodbury, MN (US); Stefan H. Gryska, Woodbury, MN (US); Robert A. Asmus, Hudson, WI (US); Melvin Y. Wong, Eagan, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/028,488

(22) Filed: Jul. 6, 2018

(65) Prior Publication Data

US 2018/0313802 A1    Nov. 1, 2018

Related U.S. Application Data

(63) Continuation of application No. 14/915,692, filed as application No. PCT/US2014/055431 on Sep. 12, 2014, now Pat. No. 10,041,920.

(Continued)

(51) Int. Cl.
*G01N 33/00* (2006.01)
*A61B 5/145* (2006.01)
(Continued)

(52) U.S. Cl.
CPC ....... *G01N 33/0047* (2013.01); *A61B 5/1477* (2013.01); *A61B 5/14546* (2013.01);
(Continued)

(58) Field of Classification Search
CPC .......... G01N 33/0009; G01N 33/0027; G01N 33/0047; G01N 33/4972; A61B 5/4845;
(Continued)

(56) References Cited

U.S. PATENT DOCUMENTS

| 5,944,661 A | 8/1999 | Swette |
| 5,952,924 A | 9/1999 | Evans |

(Continued)

FOREIGN PATENT DOCUMENTS

| JP | S62-214336 A | 9/1987 |
| JP | 2002263072 A | 9/2002 |

(Continued)

OTHER PUBLICATIONS

"FDA Safety Communications: Preventing Surgical Fires", U.S. Food and Drug Administration, Oct. 13, 2011, 3 pgs.

(Continued)

*Primary Examiner* — Benjamin R Schmitt
(74) *Attorney, Agent, or Firm* — Yuefeng Dong

(57) ABSTRACT

A vapor sensor comprises a housing with an inlet opening in fluid communication with a sensor element within the housing. Standoff member(s) are positioned to maintain a gap between the inlet opening and a skin site. An operating circuit is in electrical communication with the sensor element and communicatively coupled to an output member. In use, the output member generates a sensory output indicative to an operator regarding concentration of alcoholic vapor in the ambient atmosphere proximate the skin site upon receiving communication from the operating circuit.

20 Claims, 5 Drawing Sheets

Related U.S. Application Data

(60) Provisional application No. 61/882,710, filed on Sep. 26, 2013.

(51) Int. Cl.
*A61B 5/1477* (2006.01)
*A61B 5/00* (2006.01)
*G01D 11/24* (2006.01)
A61B 10/00 (2006.01)
G01N 33/497 (2006.01)

(52) U.S. Cl.
CPC .......... *A61B 5/4845* (2013.01); *G01D 11/245* (2013.01); *A61B 5/44* (2013.01); *A61B 10/0064* (2013.01); *A61B 2010/0083* (2013.01); *G01N 33/4972* (2013.01)

(58) Field of Classification Search
CPC .. A61B 5/44; A61B 5/68; A61B 5/683; A61B 5/70; A61B 5/742; A61B 2010/0083; G01D 11/245
USPC .......................... 73/31.05; 600/306, 382, 386
See application file for complete search history.

(56) References Cited

U.S. PATENT DOCUMENTS

| | | | | |
|---|---|---|---|---|
| 6,162,218 | A | * | 12/2000 | Elbrecht .............. A61B 18/203 606/41 |
| 6,345,191 | B1 | * | 2/2002 | Hartmann .......... A61B 5/14552 422/80 |
| 7,616,122 | B2 | | 11/2009 | Bolling |
| 2006/0058784 | A1 | | 3/2006 | Gedebou |
| 2006/0154377 | A1 | | 7/2006 | Lambert et al. |
| 2006/0246273 | A1 | | 11/2006 | McKeown |
| 2007/0173710 | A1 | * | 7/2007 | Petisce ................ A61B 5/14532 600/345 |
| 2008/0009693 | A1 | * | 1/2008 | Hawthorne ............ A61B 5/097 600/364 |
| 2008/0042854 | A1 | | 2/2008 | Bolling |
| 2010/0277740 | A1 | | 11/2010 | Hulteen |
| 2010/0300708 | A1 | | 12/2010 | Raphael |
| 2011/0031983 | A1 | * | 2/2011 | David ................... G01N 27/125 324/663 |
| 2011/0045601 | A1 | | 2/2011 | Gryska |
| 2011/0206378 | A1 | | 8/2011 | Bolling |
| 2012/0046571 | A1 | | 2/2012 | Varpula |
| 2013/0006066 | A1 | | 1/2013 | Melton |
| 2013/0098365 | A1 | | 4/2013 | Bohner |
| 2014/0303462 | A1 | * | 10/2014 | Ellenberger-Girard ...................... A61B 5/6833 600/314 |

FOREIGN PATENT DOCUMENTS

| | | |
|---|---|---|
| JP | 2003213558 A | 7/2003 |
| JP | 2010151659 A | 7/2010 |
| JP | 2012198060 A | 10/2012 |
| JP | 2010-281698 A | 2/2013 |
| WO | WO 1996-07901 | 3/1996 |
| WO | WO 2005-012397 | 2/2005 |
| WO | WO 2007/001866 | 1/2007 |
| WO | WO 2007-149391 | 12/2007 |
| WO | WO 2009-045733 | 4/2009 |
| WO | WO 2010/075333 | 7/2010 |
| WO | WO 2011-123409 | 10/2011 |
| WO | WO 2012-044419 | 4/2012 |
| WO | WO 2012-050686 | 4/2012 |
| WO | WO 2012-141883 | 10/2012 |
| WO | WO 2012-141894 | 10/2012 |
| WO | WO 2012-141925 | 10/2012 |
| WO | WO 2012-141958 | 10/2012 |
| WO | WO 2012-174099 | 12/2012 |
| WO | WO 2013-090188 | 6/2013 |

OTHER PUBLICATIONS

"The Patient is on Fire! A Surgical Fires Primer", ECRI Guidance 21, Jan. 1992, pp. 19-34.
Biovigil "Hand Hygiene Solutions simplified", 2 pgs.
Briscoe, "Inflammable Antiseptics and Theatre Fires", British Journal of Surgery, 1976, vol. 63, pp. 981-983.
Bruley, "Surgical Fires: Perioperative Communication is essential to Prevent this Rare but Devastating Complication", Quality and Safety in Health Care, Dec. 2004, vol. 13, No. 6, pp. 467-471.
Budd, "Free Volume and Intrinsic Microporosity in Polymers", Journal of Materials Chemistry, 2005, vol. 15, pp. 1977-1986.
Budd, "Polymers of Intrinsic Microporosity (PIMs): Robust, Solution-Processable, Organic Nanoporous Materials", Chemical Communications, 2004, pp. 230-231.
Carta, "Novel Spirobisindanes for Use as Precursors to Polymers of Intrinsic Microporosity", Organic Letters, 2008, vol. 10, No. 13, pp. 2641-2643.
Dunn, "UF Spin-off Xhale Innovations' HyGreen System Makes Sure Health-care Workers Wash Their Hands", Sniffing Out Germs, 2010, pp. 30-35.
Edmond, "Successful Use of Alcohol Sensor Technology to Monitor and Report Hand Hygiene Compliance", Letters to the Editor/ Journal of Hospital Infection, 2010, vol. 76, pp. 364-365.
Ghanem, "High-Performance Membranes from Polyimides with Intrinsic Microporosity", Advanced Materials, 2008, vol. 20, pp. 2766-2771.
Ghanem, "Polymers of Intrinsic Microporisity Derived from Bis(phenazyl) Monomers", Macromolecules, 2008, vol. 41, pp. 1640-1646.
Hart, "Operating Room Fire Safety", The Ochsner Journal, 2011, vol. 11, pp. 37-42.
Herman, "Surgical Fire During Organ Procurement", The Internet Journal of Anesthesiology, 2009, vol. 19, No. 1, 3 pgs.
Hibbard, "Analyses Comparing the Antimicrobial Activity and Safety of Current Antiseptic Agents: A Review", Journal of Infusion Nursing, May/Jun. 2005, vol. 28, No. 3, pp. 194-207.
"Hospital Seek High-tech help for Hand Hygiene", Jun. 20, 2013, 2pgs.
Mckeown, "Polymers of Intrinsic Microporosity (PIMS): Bridging the Void between Microporous and Polymeric Materials", Chemistry A European Journal, 2005, vol. 11, pp. 2610-2620.
Rocos, "Alcohol Skin Preparation Causes Surgical Fires", Annals of the Royal College of Surgeons of England, Mar. 2012, vol. 94, No. 2, pp. 87-89.
Rotter M. (1999). "Hand washing and hand disinfection". Hospital epidemiology and infection control chapter 87, $2^{nd}$ edition.
Staples, "Detection of Ethanol in Water and Air Using the zNose", Electronic Sensor Technology, 11 pgs.
Tooher, "Surgical Fires and Alcohol-Based Skin Preparations", ANZ Journal of Surgery, May 2004, vol. 74, No. 5, pp. 382-385.
Yardley, "Surgical Fires, a Clear and Present Danger", The Surgeon, 2010, vol. 8, No. 2, pp. 87-92.
International Search Report for PCT International Application No. PCT/US2014/055431, dated Dec. 2, 2014, 4pgs.
Gifu University Hospital *Efforts for measures to prevent infection related to vascular catheters*, 3M(TM) Tegaderm TMFilm Dressing Letter 2, 3M Health Care Limited, Dec. 2012.

\* cited by examiner

VAPOR SENSOR SUITABLE FOR DETECTING ALCOHOLIC RESIDUE AT A SKIN SITE

FIELD

The present disclosure relates to sensors for detecting environmental chemical vapors, and methods of using them.

BACKGROUND

Antimicrobial preparations including ethyl alcohol or isopropyl alcohol for skin disinfection are commonly used prior to catheter installations. Residual vapors from such alcohol-based preparations can compromise the effectiveness of adhesive tapes and dressings that are then applied to further prepare the site and/or fix the catheter. Further, inadequate drying of the skin prior to application of drapes and dressings also increases the patient's risk of skin irritation.

One typical protocol is to require a three-minute waiting period after applying alcohol-based antimicrobial preparations before applying further materials or devices to treated skin. This period is not always followed due to burdens on the nursing staff. Even if the time is allowed, it does not ensure that the risks have been removed in all conditions. For example, alcohol-based preparations may have inadvertently pooled in a hard-to-see location, requiring an even longer time to evaporate.

SUMMARY

In one aspect, the present disclosure provides a vapor sensor for detecting alcoholic residue at a skin site, the vapor sensor comprising:
a housing, wherein the housing comprises an inlet opening extending to the interior of the housing;
a sensor element disposed within the housing and in fluid communication with the inlet opening, wherein the sensor element comprises a first conductive member, a second conductive member, and an absorptive dielectric material sandwiched between the first conductive member and the second conductive member;
at least one standoff member disposed proximate to the housing, wherein the at least one standoff member is positioned to maintain a gap between the inlet opening and the skin site;
an operating circuit in electrical communication with the sensor element and capable of detecting a parameter of the sensor element, wherein the parameter correlates with alcohol concentration; and
at least one output member communicatively coupled to the operating circuit, wherein the at least one output member is adapted to generate a sensory output indicative to an operator regarding concentration of alcoholic vapor in the ambient atmosphere proximate the skin site upon receiving communication from the operating circuit.

In another aspect, the present disclosure provides a method of detecting alcohol residue, the method comprising:
providing a vapor sensor for detecting alcoholic residue at a skin site, the vapor sensor comprising:
a housing, wherein the housing comprises an inlet opening extending to the interior of the housing;
a sensor element disposed within the housing and in fluid communication with the inlet opening;
a sensor element disposed within the housing and in fluid communication with the inlet opening, wherein the sensor element comprises a first conductive member, a second conductive member, and an absorptive dielectric material sandwiched between the first conductive member and the second conductive member;
at least one standoff member disposed proximate to the housing, wherein the at least one standoff member is positioned to maintain a gap between the inlet opening and the skin site;
an operating circuit in electrical communication with the sensor element and capable of detecting a parameter of the sensor element, wherein the parameter correlates with alcohol concentration; and
at least one output member communicatively coupled to the operating circuit, wherein the at least one output member is adapted to generate a sensory output indicative to an operator regarding concentration of alcoholic vapor in the ambient atmosphere proximate the skin site upon receiving communication from the operating circuit;
placing the vapor sensor proximate to a skin site such that the inlet opening is separated from the skin site by the at least one standoff member;
introducing the ambient atmosphere proximate the skin site into the inlet opening such that the sensor element is exposed to the ambient atmosphere;
measuring a value of the parameter of the sensor element; and
based at least in part on the value of the parameter, causing the at least one output member to generate the sensory output.

Advantageously, vapor sensors according to the present disclosure may be fabricated in portable configurations (e.g., handheld models) that are relatively inexpensive and maintenance free, and provide easy to understand indication that alcohol vapors are below an acceptable threshold level to prevent skin irritation and/or adhesion problems.

As used herein, the term "absorptive" includes absorption as well as adsorption that occurs on the sides of interior voids in a material (e.g., a microporous polymer).

Unless otherwise specified, the term "alcohol" (as well as "alcoholic" and "alcohol-based") refers to ethanol and/or isopropanol.

As used herein, the term "skin site" refers to animal skin (e.g., human skin) at or proximate to a pre-surgical or pre-procedural (e.g., pre-catheter insertion) site.

Features and advantages of the present disclosure will be further understood upon consideration of the detailed description as well as the appended claims.

Figure 1A:
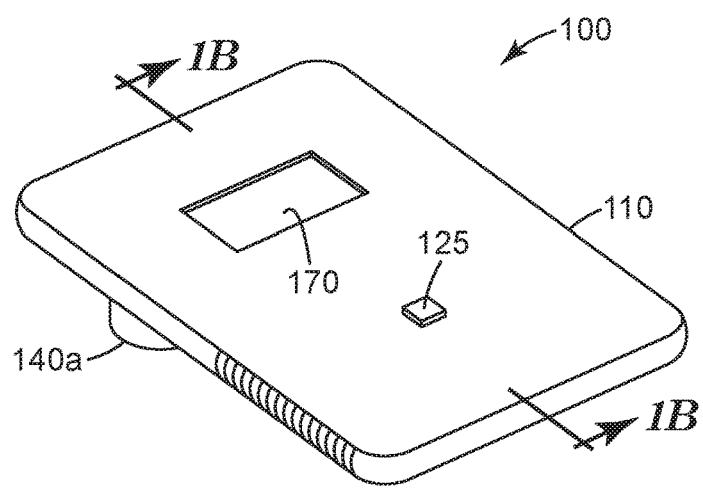
FIG. 1A is a schematic perspective view of exemplary vapor sensor 100 according to the present disclosure.

Repeated use of reference characters in the specification and drawings is intended to represent the same or analogous features or elements of the disclosure. It should be understood that numerous other modifications and embodiments can be devised by those skilled in the art, which fall within the scope and spirit of the principles of the disclosure. The figures may not be drawn to scale.

DETAILED DESCRIPTION

Figure 1B:
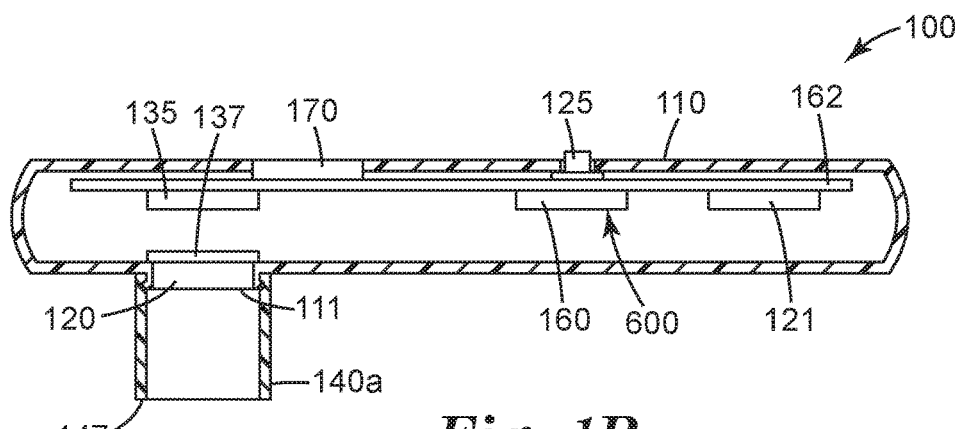
FIG. 1B is a schematic cross-sectional view of exemplary vapor sensor 100 shown in FIG. 1A taken along plane 1B-1B.
Figure 1C:
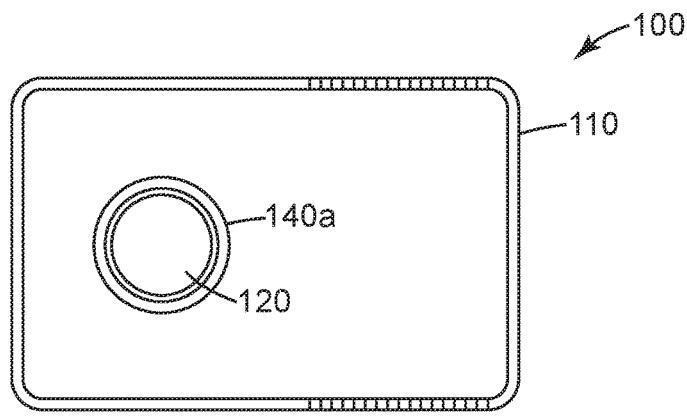
FIG. 1C is a schematic bottom view of exemplary vapor sensor 100.
Figure 5A:
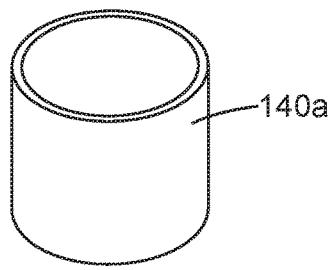
FIGS. 5A-5D are schematic perspective views of tubular standoff members 140a, 140b, 140c, and 140d, respectively.

FIGS. 1A-1C illustrate an exemplary vapor sensor for detecting alcoholic residue at a skin site according to the present disclosure. Referring to FIGS. 1A-1C, vapor sensor 100 includes housing 110 with inlet opening 120. Sensor element 135 is disposed within housing 110 and is in fluid communication with inlet opening 120. Tubular standoff member 140a (shown in perspective in FIG. 5A) is mounted to housing 110 by a press fit to circular boss 111 around inlet opening 120, although it is contemplated that other attachment methods such as mechanical fasteners or adhesives may also be used. Optional porous filter 137 covers inlet opening 120 to block dust from entering the vapor sensor. Tubular standoff member 140a consists of a tube with no holes slits or notches in the tube wall. While shown as a press fit separate part, tubular standoff member alternatively may be integrally formed with the housing. Alternative designs of tubular standoff members are shown in FIGS. 5B-5D.

Figure 5B:
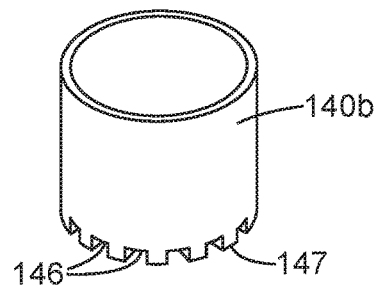

Referring to FIG. 5B, tubular standoff member 140b has a plurality of notches 146 proximate its distal opening 147 when mounted onto the vapor sensor. A single notch may also be used.

Figure 5C:
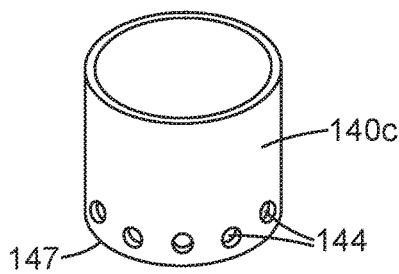

Referring to FIG. 5C, tubular standoff member 140c has a plurality of round holes 144 (i.e., through the wall of the tube) proximate its distal opening 147 when mounted onto the vapor sensor. A single round hole may also be used.

Figure 5D:
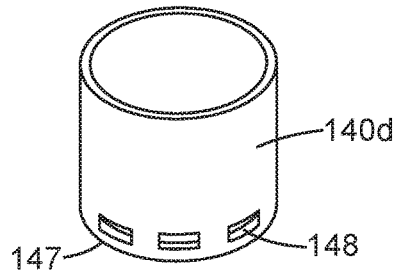

Referring to FIG. 5D, tubular standoff member 140d has a plurality of slots 148 proximate its distal opening 147 when mounted onto the vapor sensor. A single slot may also be used.

Standoff members (including tubular standoff members) may have a length of from 0.25 inch (0.66 cm) to 30 inches (76 cm), preferably from 10 inches (25 cm) to 14 inches (36 cm), and more preferably about 12 inches, (30 cm), although this is not a requirement.

If supplied as a disposable or reusable part, tubular standoff members may be conveniently delivered sterile inside a protective pouch. Tubular standoff members may be conveniently made of readily disposable material such as, for example, stiff cardboard or a low cost polymer such as polyethylene or polypropylene. Similarly, the entire vapor sensor may be supplied in a disposable sterile package, for example.

Referring again to FIG. 1B, operating circuit 160, which is supported on circuit board 162, is in electrical communication with the sensor element 135 and is capable of measuring the value of a parameter such as, for example, capacitance, reflectance, or conductance, depending on the type of sensor element selected. Output member 170 is communicatively coupled to operating circuit 160. Operating circuit 160 is powered by battery 121. In response to receiving a communication from operating circuit 160, a textual indicator appears on output member 170 (shown in FIGS. 1A-1C as a liquid crystal display (LCD)), thereby indicating whether the concentration of residual alcohol is within acceptable limits for achieving a good adhesion to pressure-sensitive adhesive articles (e.g., tapes, patches, bandages, dressings, or electrical leads). On/off switch 125 (operator controls) activates vapor sensor 100. While a circuit board is shown in this embodiment, it is also contemplated that the components could be mounted separately (e.g., to the housing) and can be connected by wires instead of circuit traces on the circuit board, for example.

Figure 4:
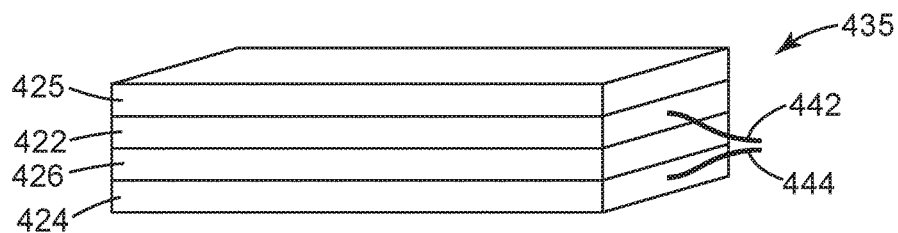
FIG. 4 is a schematic perspective view of exemplary capacitive sensor element 435.

Sensor element 135 may be any type of sensing device capable to measuring alcohol vapor (e.g., capacitance sensor elements, optoelectronic sensor elements, surface plasmon resonance sensor elements, surface acoustic wave sensor elements, photoionization sensor elements, or conductance sensor elements). In some preferred embodiments, sensor element 135 is a capacitive sensor element 435 (see FIG. 4) comprising first and second conductive members (422, 424) with absorptive dielectric material 426 disposed therebetween. First conductive member is supported on dielectric substrate 425 (e.g., a dielectric plastic film). Second conductive member 424 is preferably sufficiently porous (e.g., a thermal vapor deposited metal film or printed conductive nanoparticle ink) to permit alcohol vapor to easily penetrate. Capacitive sensor element 435 is shown with its associated leads 442 and 444, which attach to first and second conductive members 422 and 424, respectively. While shown here as plates, the first and second conductive members may have other configurations (e.g., interdigitated electrical traces) as is known in the capacitance sensor art.

If desired, the vapor sensor may be configured such that the sensor element can be readily replaced by a user without opening the housing. For example, the sensor element may be replaceable through a slot in the housing.

The first conductive member can comprise any suitable conductive material. Combinations of different materials (conductive and/or nonconductive) can be used, as different layers or as a mixture, as long as sufficient overall conductivity is provided. Typically, the first conductive member has a sheet resistance of less than about $10^7$ ohms/square. Examples of materials that can be used to make the first conductive member and/or second conductive member include organic materials, inorganic materials, metals, alloys, and various mixtures and composites comprising any or all of these materials. In certain embodiments, coated (for example, thermal vapor coated or sputter coated) metals or metal oxides, or combinations thereof, may be used. Suitable conductive materials include for example aluminum, nickel, titanium, tin, indium-tin oxide, gold, silver, platinum, palladium, copper, chromium, carbon nanotubes, and combinations thereof. In certain embodiments, the first conductive member may also be formed by printing a metallic ink (e.g., a silver ink or a gold ink), followed by drying the ink.

Second conductive member need not be permeable by alcohol vapor, although it preferably is. Examples of materials that can be used to make the second conductive member include organic materials, inorganic materials, metals, alloys, and various mixtures and composites comprising any or all of these materials. In certain embodiments, coated (for example, thermal vapor coated, sputter coated, etc.) metals or metal oxides, or combinations thereof, may be used. Suitable conductive materials include for example aluminum, nickel, titanium, tin, indium-tin oxide, gold, silver, platinum, palladium, copper, chromium, carbon nanotubes, and combinations thereof. In certain embodiments, the second conductive member 424 may also be formed by printing a metallic ink (e.g., a silver ink or a gold ink), followed by drying the ink. Combinations of different materials (conductive and/or nonconductive) can be used, as different layers or as a mixture, as long as sufficient overall conductivity and permeability is provided. Typically, second conductive member 424 has a sheet resistance of less than about $10^7$ ohms/square.

The first conductive member can be of any thickness as long as it is conductive; for example, in a thickness in a range of from at least 4 nanometers (nm) to 400 nm, or from 10 nm to 200 nm.

In some embodiments, the first conductive member may follow a tortuous path and may optionally serve as a heating element; for example, as described in PCT International Appl. Publ. No. WO 2012/141958 A1 (Palazzotto et al.); however, this is not a requirement, and other configurations are also contemplated. A tortuous path typically serves to increase the area that may be heated and/or increase the rate of heating.

The second conductive member typically has a thickness in a range of from 1 nm to 100 micrometers, although other thicknesses may be used.

For example, the second conductive member may have a thickness in a range of from 1 nm to 100 nm, or even from 4 nm to 10 nm. Greater thicknesses may have undesirably low levels of permeability, while lesser thicknesses may become insufficiently conductive and/or difficult to electrically connect to the second conductive member.

In another embodiment, the first and second conductive members may be disposed side-by-side on the surface of the dielectric substrate (e.g., within a single plane), separated by the absorptive dielectric material. In this embodiment, the second conductive member need not be permeable by the analyte vapor. In such a case, the second conductive member may be fabricated using a material suitable for use as the first conductive member.

The absorptive dielectric material is preferably a material that is microporous and is capable of absorbing at least one analyte within its interior. In this context, the terms "microporous" and "microporosity" mean that the material has a significant amount of internal, interconnected pore volume, with the mean pore size (as characterized, for example, by sorption isotherm procedures) being less than about 100 nm, typically less than about 10 nm. Such microporosity provides that molecules of organic analyte (if present) will be able to penetrate the internal pore volume of the material and take up residence in the internal pores. The presence of such analyte in the internal pores can alter the dielectric properties of the material such that a change in the dielectric constant (or any other suitable electrical property) can be observed.

In some embodiments, the absorptive dielectric material comprises a so-called Polymer of Intrinsic Microporosity (PIM). PIMs are polymeric materials with nanometer-scale pores due to inefficient packing of the polymer chains. For example, in *Chemical Communications*, 2004, (2), pp. 230-231, Budd et al. report a series of intrinsically microporous materials containing dibenzodioxane linkages between rigid and/or contorted monomeric building blocks. Representative members of this family of polymers include those generated by condensation of Component A (e.g., A1, A2, or A3) with Component B (e.g., B1, B2, or B3) as shown in Table 1 according to Scheme 1 (below).

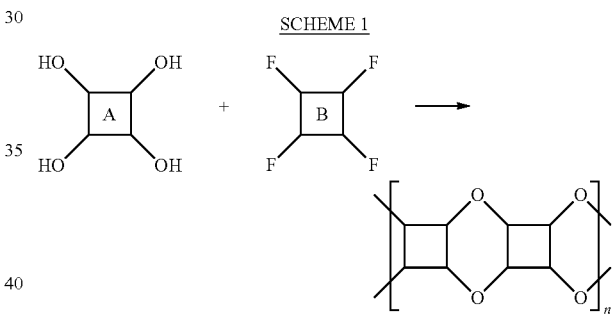

SCHEME 1

TABLE 1

| COMPONENT A | COMPONENT B |
|---|---|
| A1 | B1 |

TABLE 1-continued

| COMPONENT A | COMPONENT B |
|---|---|

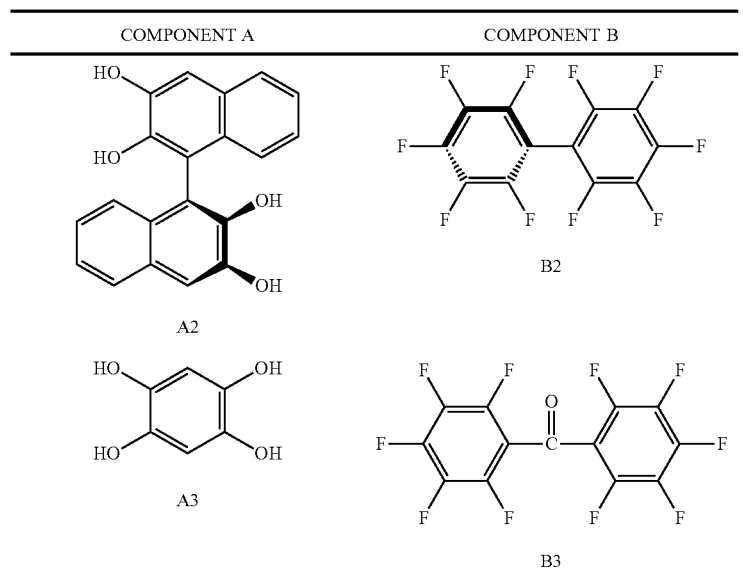

Further suitable Components A and B, and resultant intrinsically microporous polymers, are known in the art, for example, as reported by Budd et al. in *Journal of Materials Chemistry*, 2005, Vol. 15, pp. 1977-1986; by McKeown et al. in *Chemistry, A European Journal*, 2005, Vol. 11, pp. 2610-2620; by Ghanem et al. in *Macromolecules*, 2008, vol. 41, pp. 1640-1646; by Ghanem et al. in *Advanced Materials*, 2008, vol. 20, pp. 2766-2771; by Carta et al. in *Organic Letters*, 2008, vol. 10(13), pp. 2641-2643; in PCT Published Application WO 2005/012397 A2 (McKeown et al.); and in U.S. Patent Appl. Publ. No. 2006/0246273 (McKeown et al.). Such polymers can be synthesized, for example, by a step-growth polymerization where a bis-catechol such as, e.g., A1 (5,5',6,6'-tetrahydroxy-3,3,3',3'-tetramethyl-1,1'-spirobisindane) is allowed to react with a fluorinated arene such as, e.g., B1 (tetrafluoroterephthalonitrile) under basic conditions. Due to the rigidity and contorted nature of the backbone of the resulting polymers, these polymers are unable to pack tightly in the solid state and thus have at least 10 percent free volume and are intrinsically microporous.

PIMs may be blended with other materials. For example, a PIM may be blended with a material that itself is not an absorptive dielectric material. Even though not contributing to an analyte response, such a material may be useful for other reasons. For example, such a material may allow the formation of a PIM-containing layer which has superior mechanical properties and the like. In one embodiment, PIMs may be dissolved in a common solvent with the other material to form a homogeneous solution, which may be cast to form an absorptive dielectric blend layer comprising both the PIM and the other polymer(s). PIMs may also be blended with a material that is an absorptive dielectric material (for example, zeolites, activated carbon, silica gel, hyper-crosslinked polymer networks and the like). Such materials may comprise insoluble materials that are suspended in a solution comprising of a PIMs material. Coating and drying of such a solution/suspension may provide a composite absorptive dielectric layer comprising both the PIM material and the additional absorptive dielectric material.

PIMs are typically soluble in organic solvents such as, for example, tetrahydrofuran and can thus be cast as films from solution (e.g., by spin-coating, dip coating, or bar coating). However, characteristics (accessible thicknesses, optical clarity, and/or appearance) of films made from solutions of these polymers may vary markedly depending on the solvent or solvent system used to cast the film. For example, intrinsically microporous polymers of higher molecular weights may need to be cast from relatively unusual solvents (e.g., cyclohexene oxide, chlorobenzene, or tetrahydropyran) to generate films with desirable properties for use in vapor sensors as described herein. In addition to solution coating methods, the detection layer may be applied to the first conductive member by any other suitable method.

After a PIM is deposited (e.g., coated) or otherwise formed so as to comprise an absorptive dielectric layer, the material may be crosslinked using a suitable crosslinking agent such as, for example, bis(benzonitrile)palladium(II) dichloride. This process may render the absorptive dielectric layer insoluble in organic solvents, and/or may enhance certain physical properties such as durability, abrasion resistance, etc., which may be desirable in certain applications.

PIMs may be hydrophobic so that they will not absorb liquid water to an extent that the material swells significantly or otherwise exhibits a significant change in a physical property. Such hydrophobic properties are useful in providing an organic analyte sensor element that is relatively insensitive to the presence of water. The material may however comprise relatively polar moieties for specific purposes.

In one embodiment, the absorptive dielectric material comprises a continuous matrix. Such a matrix is defined as an assembly (e.g., a coating, layer, etc.) in which the solid portion of the material is continuously interconnected (irrespective of the presence of porosity as described above, or of the presence of optional additives as discussed below). That is, a continuous matrix is distinguishable from an assembly that comprises an aggregation of particles (e.g., zeolites, activated carbons, or carbon nanotubes). For example, a layer or coating deposited from a solution will typically comprise a continuous matrix (even if the coating itself is applied in a patterned manner and/or comprises particulate additives). A collection of particles deposited via powder spraying, coating and drying of a dispersion (e.g., a latex), or by coating and drying of a sol-gel mixture, may not comprise a continuous network. However, if such a latex, sol-gel, etc., layer can be consolidated such that individual particles are no longer discernible, nor is it possible to discern areas of the assembly that were obtained from different particles, such a layer may then be considered to be a continuous matrix.

Capacitance sensor elements can be made, for example, by disposing the first conductive member on the dielectric substrate (e.g., by vapor deposition or by photolithography) using a method common in circuit manufacture (e.g., by vapor deposition or by photolithography).

Next, absorptive dielectric material in a suitable organic solvent is coated onto the first conductive member and the solvent removed. Finally, the second conductive member is disposed on the absorptive dielectric material (e.g., by vapor deposition or a printing method such as screen printing, using a digital printing method (e.g., ink jet printing)).

Figure 6:
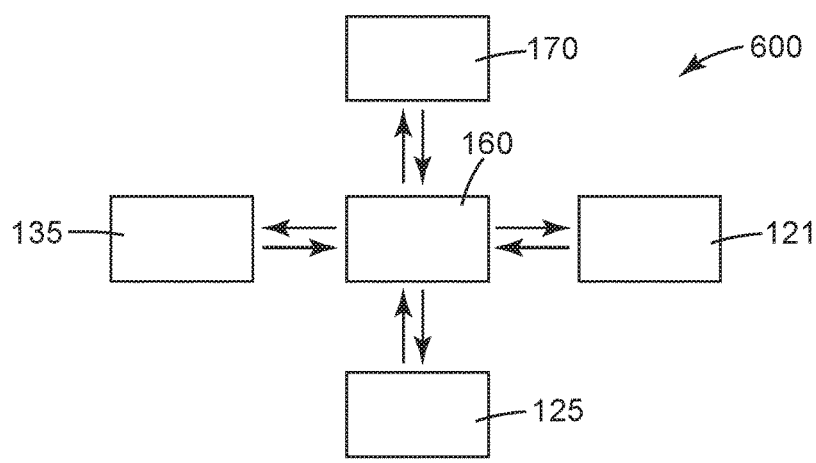
FIG. 6 is a block diagram of an exemplary circuit configuration suitable for use in vapor sensors according to the present disclosure.

FIG. 6 illustrates an exemplary operating circuit 600 configuration for coordinating the operation of sensor element 135 and output member 170. Control module 160 is electrically connected to sensor element 135. Control module 160 is communicatively coupled (e.g., by electrical circuit or through wireless communication) to at least one output member 170 and optional operator controls 125. Operating circuit is powered by an electrical source 121 (e.g., a battery or power cord). If present, optional fan 150 may also be conveniently controlled by control module 160. It will be recognized that other operating circuit configurations are permissible and within the capabilities of one of ordinary skill in the art.

Additional details concerning capacitance-type sensor elements, their fabrication, calibration, vapor sensors including them, and their use to measure organic vapor (e.g., alcohol) concentration can be found in PCT International Appl. Publ. Nos. WO 2012/141883 A1 (Palazzotto et al.), WO 2012/050686 A1 (Palazzotto et al.), WO 2012/141894 A1 (Kang et al.), WO 2013/090188 A1 (Gryska et al.), and U.S. Pat. Appln. Publ. Nos. 2011/0045601 A1 (Gryska et al.) and 2010/0277740 A1 (Hulteen et al.).

Details concerning other types of sensor elements, their fabrication, vapor sensors including them, and their use to measure organic vapor (e.g., alcohol) concentration can be found in PCT International Appl. Publ. Nos. WO 2012/174099 A1 (Kang et al., concerning surface plasmon resonance sensor elements) and PCT International Appl. Publ. Nos. WO 2012/141883 A1 (Palazzotto et al., concerning capacitance and optoelectronic sensor elements).

Figure 2A:
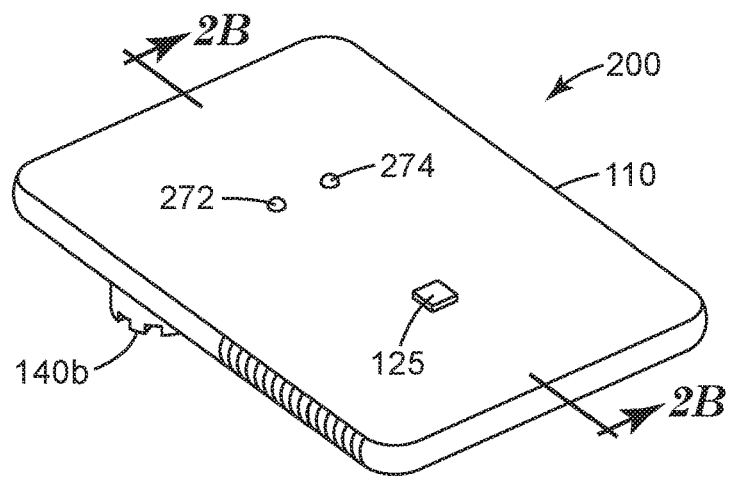
FIG. 2A is a schematic perspective view of exemplary vapor sensor 200 according to the present disclosure.
Figure 2B:
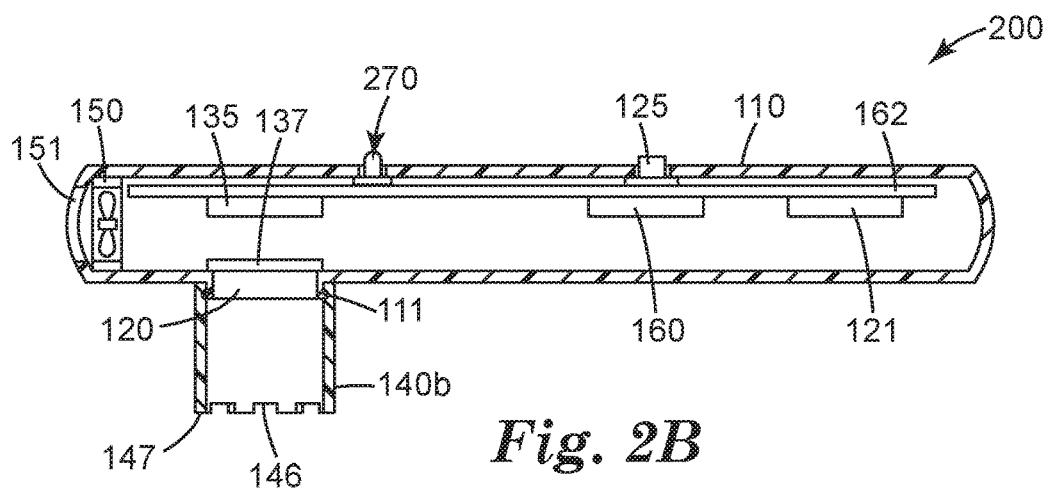
FIG. 2B is a schematic cross-sectional view of exemplary vapor sensor 200 shown in FIG. 2A taken along plane 2B-2B.
Figure 2C:
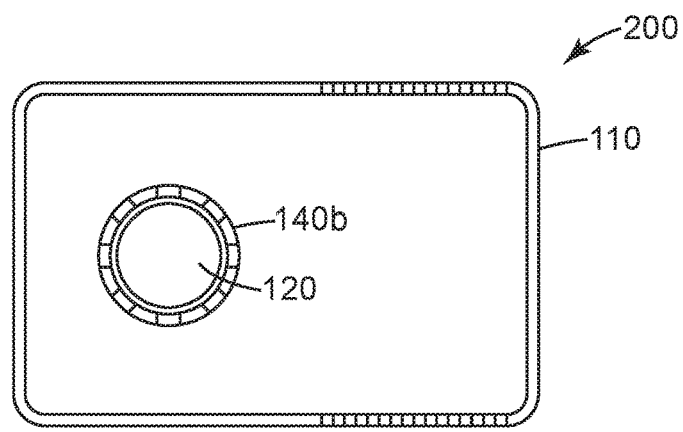
FIG. 2C is a schematic bottom view of exemplary vapor sensor 200.

FIGS. 2A-2C illustrate another embodiment of an exemplary vapor sensor for detecting alcoholic residue at a skin site according to the present disclosure. Referring to FIGS. 2A-2C, vapor sensor 200 includes housing 110 with inlet opening 120. Sensor element 135 is disposed within housing 110 and is in fluid communication with inlet opening 120. Optional porous filter 137 covers inlet opening 120 to block dust from entering the vapor sensor. Although not shown, a second porous filter covering the outlet opening may be included, although this is not a requirement. This second porous filter may be the same or similar to the porous filter covering the inlet opening, for example. Fan 150 directs air entering inlet opening 120 through the housing and out outlet opening 151. Tubular standoff member 140b (shown in perspective in FIG. 5B) is mounted to housing 110 by a press fit to circular boss 111 around inlet opening 120. Operating circuit 160 supported on circuit board 162 is in electrical communication with the sensor element 135. Operating circuit 160 is powered by battery 121. Output member 270 includes indicator lights 272 (red), 274 (green) that indicate to an operator when the alcohol concentration is acceptably low.

Figure 3A:
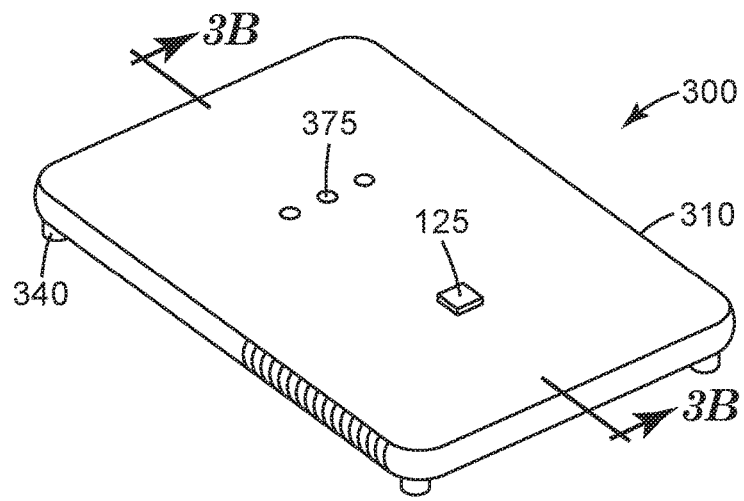
FIG. 3A is a schematic perspective view of exemplary vapor sensor 300 according to the present disclosure.
Figure 3B:
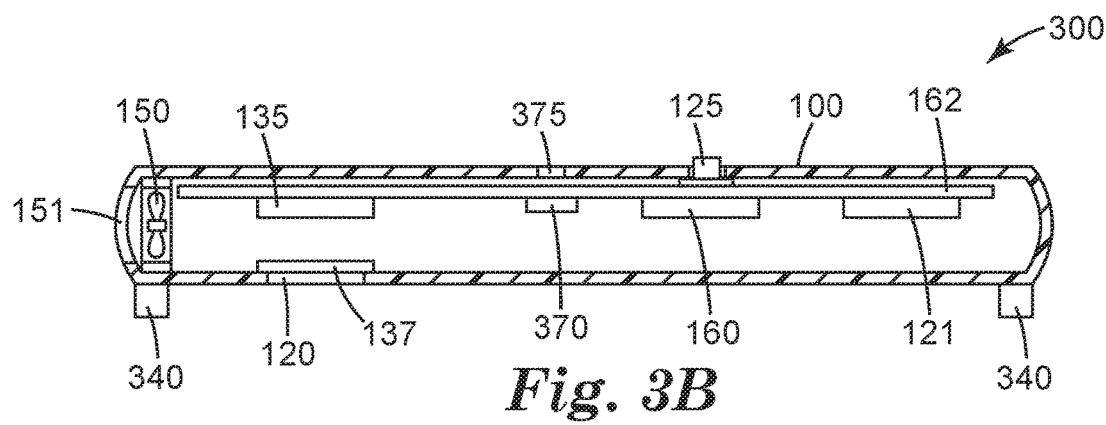
FIG. 3B is a schematic cross-sectional view of exemplary vapor sensor 300 shown in FIG. 3A taken along plane 3B-3B.
Figure 3C:
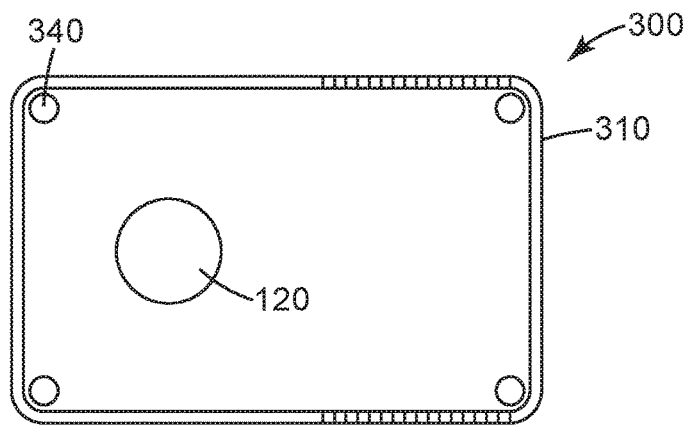
FIG. 3C is a schematic bottom view of exemplary vapor sensor 300.

FIGS. 3A-3C illustrate another embodiment of an exemplary vapor sensor for detecting alcoholic residue at a skin site according to the present disclosure. Referring to FIGS. 3A-3C, vapor sensor 300 includes housing 110 with inlet opening 120. Sensor element 135 is disposed within housing 110 and is in fluid communication with inlet opening 120. Optional porous filter 137 covers inlet opening 120 to block dust from entering the vapor sensor. Fan 150 directs air entering inlet opening 120 through the housing and out outlet opening 151. Tubular standoff members 340 are mounted to housing (e.g., by adhesive). Operating circuit 160 supported on circuit board 162 is in electrical communication with the sensor element 135. Operating circuit 160 is powered by battery 121. Output member 370 includes a sound generating device (e.g., a speaker, alarm, vibrator, or horn) that emits an audible tone through sound holes 375 that indicate to an operator that alcohol concentration is acceptably low.

Vapor sensors according to the present disclosure are useful, for example, for detecting the presence of residual alcohol at a skin site such as, for example, a pre-surgical skin site, or a pre-catheter insertion skin site. To determine alcohol presence or absence at the skin site, standoff member (s) the vapor sensor are contacted with the patient adjacent to the skin site of interest. To facilitate measurement, the skin site of interest is preferably situated as close to the inlet opening as possible. Preferably, contact is made with skin, however contact may be made with covered areas of the patient (e.g., covered by a dressing and/or clothing) if desired and/or necessary. In typical use, vapor sensors according to the present disclosure are left in contact with the skin site for sufficient time (e.g., from 1 to 10 seconds) to provide a reliable measurement of alcohol concentration. Once the detector determines that the alcohol vapor level is sufficiently low that adhesive articles can be applied to the skin site, the output module notifies the user, and the vapor sensor may be removed and adhesive dressings, tapes, and/or bandages (e.g., as associated with catheter insertion) may be applied without concern for degraded adhesion due to the presence of alcohol.

Figure 7:
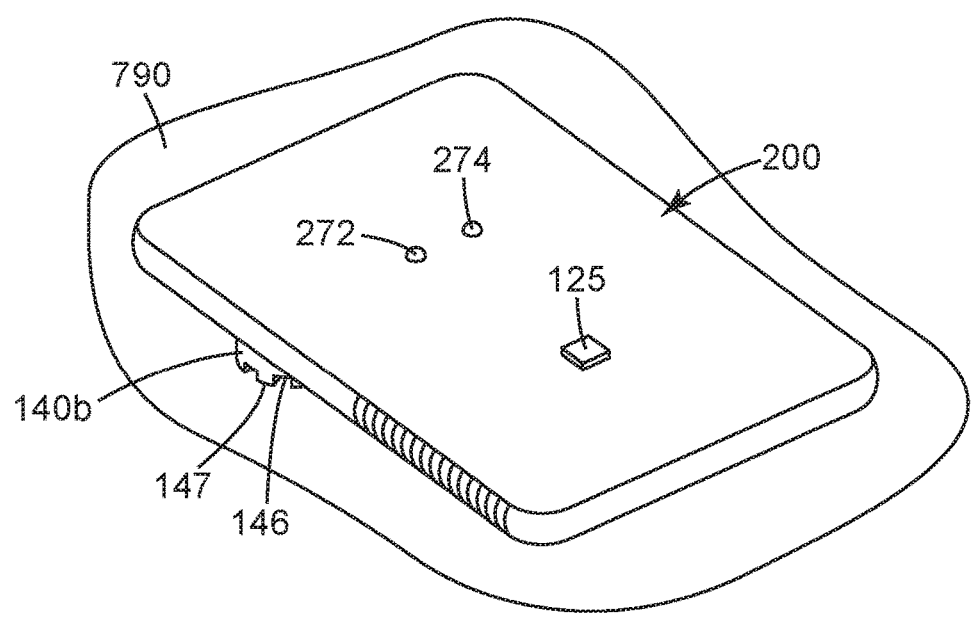
FIG. 7 shows vapor sensor 200 contacting a skin site to measure residual alcohol concentration.

FIG. 7 illustrates application and use of vapor sensor 200 to determine the level of alcohol at skin site 790, wherein notches 146 adjacent to the distal end 147 of tubular standoff member 140b permit ambient atmosphere adjacent to skin site 790 to be drawn continuously into the inlet opening by fan 150 and measured by sensor element 135 to determine alcohol vapor content in the ambient atmosphere and illumination of a red (stop) or green (proceed) indicator light depending on the alcohol vapor concentration.

The specific concentration of alcohol vapor below which a positive indication to proceed is transmitted from the vapor sensor to the operator may be any level, but preferably the level is less than about 1000 parts per million by weight or less, but this not a requirement.

Advantageously, the time required to evaluate the alcohol vapor concentration using a vapor senor according to the present disclosure may be (and typically is) minutes earlier than waiting for three minutes to elapse as in one current practice in the art.

SELECT EMBODIMENTS OF THE PRESENT DISCLOSURE

In a first embodiment, the present disclosure provides a vapor sensor for detecting alcoholic residue at a skin site, the vapor sensor comprising:

a housing, wherein the housing comprises an inlet opening extending to the interior of the housing;
a sensor element disposed within the housing and in fluid communication with the inlet opening;
at least one standoff member disposed proximate to the housing, wherein the at least one standoff member is positioned to maintain a gap between the inlet opening and the skin site;
an operating circuit in electrical communication with the sensor element and capable of detecting a parameter of the sensor element, wherein the parameter correlates with alcohol concentration; and
at least one output member communicatively coupled to the operating circuit, wherein the at least one output member is adapted to generate a sensory output indicative to an operator regarding concentration of alcoholic vapor in the ambient atmosphere proximate the skin site upon receiving communication from the operating circuit.

In a second embodiment, the present disclosure provides a vapor sensor according to the first embodiment, wherein the absorptive dielectric material comprises a polymer of intrinsic microporosity.

In a third embodiment, the present disclosure provides a vapor sensor according to the first or second embodiment, wherein the housing further comprises an outlet opening in fluid communication inside the housing with the inlet opening.

In a fourth embodiment, the present disclosure provides a vapor sensor according to the third embodiment, further comprising a device for moving gas from the inlet opening to the outlet opening.

In a fifth embodiment, the present disclosure provides a vapor sensor according to any one of the first to fourth embodiments, wherein the at least one standoff member is removably attached to the housing by a press fit.

In a sixth embodiment, the present disclosure provides a vapor sensor according to any one of the first to fifth embodiments, wherein the at least one standoff member is integral to the housing.

In a seventh embodiment, the present disclosure provides a vapor sensor according to any one of the first to sixth embodiments, wherein the at least one standoff member comprises a tube having a proximal opening, a wall, and a distal opening opposite the proximal opening, wherein the proximal opening contacts the housing and encircles the inlet port, and wherein the wall has at least one notch, at least one hole, or a combination thereof.

In an eighth embodiment, the present disclosure provides a vapor sensor according to any one of the first to sixth embodiments, wherein the at least one standoff member comprises at least three standoff members.

In a ninth embodiment, the present disclosure provides a method of detecting alcohol residue, the method comprising:
providing a vapor sensor for detecting alcoholic residue at a skin site, the vapor sensor comprising:
a housing, wherein the housing comprises an inlet opening extending to the interior of the housing;
a sensor element disposed within the housing and in fluid communication with the inlet opening;
at least one standoff member disposed proximate to the housing, wherein the at least one standoff member is positioned to maintain a gap between the inlet opening and the skin site;
an operating circuit in electrical communication with the sensor element and capable of detecting a parameter of the sensor element, wherein the parameter correlates with alcohol concentration; and
at least one output member communicatively coupled to the operating circuit, wherein the at least one output member is adapted to generate a sensory output indicative to an operator regarding concentration of alcoholic vapor in the ambient atmosphere proximate the skin site upon receiving communication from the operating circuit;
placing the vapor sensor proximate to a skin site such that the inlet opening is separated from the skin site by the at least one standoff member;
introducing the ambient atmosphere proximate the skin site into the inlet opening such that the sensor element is exposed to the ambient atmosphere;
measuring a value of the parameter of the sensor element; and
based at least in part on the value of the parameter, causing the at least one output member to generate the sensory output.

In a tenth embodiment, the present disclosure provides a method according to the ninth embodiment, wherein the skin site has been treated with an alcohol-based preparation shortly before the vapor sensor is placed proximate to the skin site.

In an eleventh embodiment, the present disclosure provides a method according to the ninth or tenth embodiment, wherein the sensor element comprises a first conductive member, a second conductive member, and an absorptive dielectric material sandwiched between the first conductive member and the second conductive member.

In a twelfth embodiment, the present disclosure provides a method according to any one of the ninth to eleventh embodiments, wherein the absorptive dielectric material comprises a polymer of intrinsic microporosity.

In a thirteenth embodiment, the present disclosure provides a method according to any one of the ninth to twelfth embodiments, wherein the housing further comprises an outlet opening in fluid communication inside the housing with the inlet opening.

In a fourteenth embodiment, the present disclosure provides a method according to the thirteenth embodiment, further comprising a device for moving gas from the inlet opening to the outlet opening.

In a fifteenth embodiment, the present disclosure provides a method according to any one of the ninth to fourteenth embodiments, wherein the at least one standoff member is removably attached to the housing by a press fit.

In a sixteenth embodiment, the present disclosure provides a method according to any one of the ninth to fifteenth embodiments, wherein the at least one standoff member is integral to the housing.

In a seventeenth embodiment, the present disclosure provides a method according to any one of the ninth to sixteenth embodiments, wherein the at least one standoff member comprises a tube having a proximal opening, a wall, and a distal opening opposite the proximal opening, wherein the proximal opening contacts the housing and encircles the inlet port, and wherein the wall has at least one notch, at least one hole, or a combination thereof.

In an eighteenth embodiment, the present disclosure provides a method according to any one of the ninth to seventeenth embodiments, wherein the at least one standoff member comprises at least three standoff members.

All cited references, patents, or patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A vapor sensor for detecting alcoholic residue at a skin site, the vapor sensor comprising:
    a housing, wherein the housing comprises an inlet opening extending to the interior of the housing;
    a sensor element disposed within the housing and in fluid communication with the inlet opening, wherein the sensor element comprises a first conductive member, a second conductive member, and an absorptive dielectric material sandwiched between the first conductive member and the second conductive member;
    at least one standoff member disposed proximate to the housing, wherein the at least one standoff member is positioned to maintain a gap between the inlet opening and the skin site, and the at least one standoff member comprises a tube having a proximal opening, a wall, and a distal opening opposite the proximal opening, the proximal opening contacts the housing and encircles the inlet opening, and the wall has one or more openings proximate the distal opening to allow ambient atmosphere adjacent to the skin site to be drawn through the wall into the inlet opening;
    an operating circuit in electrical communication with the sensor element and capable of detecting a parameter of the sensor element, wherein the parameter correlates with alcohol concentration; and
    at least one output member communicatively coupled to the operating circuit, wherein the at least one output member is adapted to generate a sensory output indicative to an operator regarding concentration of alcoholic vapor in the ambient atmosphere proximate the skin site upon receiving communication from the operating circuit.

2. The vapor sensor according to claim 1, wherein the absorptive dielectric material comprises a polymer of intrinsic microporosity.

3. The vapor sensor according to claim 1, wherein the housing further comprises an outlet opening in fluid communication inside the housing with the inlet opening.

4. The vapor sensor according to claim 3, further comprising a device for moving gas from the inlet opening to the outlet opening.

5. The vapor sensor according to claim 1, wherein the at least one standoff member is removably attached to the housing by a press fit.

6. The vapor sensor according to claim 1, wherein the at least one standoff member is integral to the housing.

7. The vapor sensor according to claim 1, wherein the one or more openings of the wall include at least one notch, at least one hole, or a combination thereof.

8. The vapor sensor according to claim 1, wherein the at least one standoff member comprises at least three standoff members.

9. A method of detecting alcohol residue, the method comprising:
    providing a vapor sensor for detecting alcoholic residue at a skin site, the vapor sensor comprising:
        a housing, wherein the housing comprises an inlet opening extending to the interior of the housing;
        a sensor element disposed within the housing and in fluid communication with the inlet opening;
        at least one standoff member disposed proximate to the housing, wherein the at least one standoff member is positioned to maintain a gap between the inlet opening and the skin site, and the at least one standoff member comprises a tube having a proximal opening, a wall, and a distal opening opposite the proximal opening, the proximal opening contacts the housing and encircles the inlet opening, and the wall has one or more openings proximate the distal opening to allow ambient atmosphere adjacent to the skin site to be drawn through the wall into the inlet opening;
        an operating circuit in electrical communication with the sensor element and capable of detecting a parameter of the sensor element, wherein the parameter correlates with alcohol concentration; and
        at least one output member communicatively coupled to the operating circuit, wherein the at least one output member is adapted to generate a sensory output indicative to an operator regarding concentration of alcoholic vapor in the ambient atmosphere proximate the skin site upon receiving communication from the operating circuit;
    placing the vapor sensor proximate to a skin site such that the inlet opening is separated from the skin site by the at least one standoff member;
    introducing the ambient atmosphere proximate the skin site through the openings of the wall into the inlet opening such that the sensor element is exposed to the ambient atmosphere;
    measuring a value of the parameter of the sensor element; and
    based at least in part on the value of the parameter, causing the at least one output member to generate the sensory output.

10. The method according to claim 9, wherein the skin site has been treated with an alcohol-based preparation shortly before the vapor sensor is placed proximate to the skin site.

11. The method according to claim 9, wherein the sensor element comprises a first conductive member, a second conductive member, and an absorptive dielectric material sandwiched between the first conductive member and the second conductive member.

12. The method according to claim 9, wherein the absorptive dielectric material comprises a polymer of intrinsic microporosity.

13. The method according to claim 9, wherein the housing further comprises an outlet opening in fluid communication inside the housing with the inlet opening.

14. The method according to claim 13, further comprising a device for moving gas from the inlet opening to the outlet opening.

15. The method according to claim 9, wherein the at least one standoff member is removably attached to the housing by a press fit.

16. The method according to claim 9, wherein the at least one standoff member is integral to the housing.

17. The method according to claim 9, wherein the one or more openings of the wall include at least one notch, at least one hole, or a combination thereof.

18. The method according to claim 9, wherein the at least one standoff member comprises at least three standoff members.

19. The method according to claim 9, wherein the skin site includes a pre-surgical skin site, or a pre-catheter insertion skin site.

20. The method according to claim 9, wherein when the sensor determines, based on the measured value, that an alcohol vapor level of the alcoholic residue at the skin site is sufficiently low that an adhesive article can be applied to the skin site, the output member notifies a user to remove the vapor sensor and apply the adhesive article.

* * * * *